(12) United States Patent
Koblanski

(10) Patent No.: US 7,503,898 B2
(45) Date of Patent: Mar. 17, 2009

(54) METHODS OF AND APPARATUS FOR MONITORING HEART MOTIONS

(76) Inventor: John Koblanski, 102-2108 38 Avenue West, Vancouver, Bristish Columbia (CA) V6M 1R9

(*) Notice: Subject to any disclaimer, the term of this patent is extended or adjusted under 35 U.S.C. 154(b) by 570 days.

(21) Appl. No.: 11/207,704

(22) Filed: Aug. 22, 2005

(65) Prior Publication Data

US 2007/0043300 A1    Feb. 22, 2007

(51) Int. Cl.
   *A61B 5/02* (2006.01)
(52) U.S. Cl. ..................... 600/527; 600/508
(58) Field of Classification Search .......... 600/527, 600/528
   See application file for complete search history.

(56) References Cited

U.S. PATENT DOCUMENTS

| 2,141,246 | A | * | 12/1938 | Jacobus et al. | 600/527 |
| 4,945,916 | A | * | 8/1990 | Kretschmer et al. | 600/484 |
| 5,865,759 | A | | 2/1999 | Koblanski | |
| 6,517,492 | B2 | | 2/2003 | Koblanski | |
| 2005/0154285 | A1 | | 7/2005 | Neason | |

* cited by examiner

*Primary Examiner*—Kennedy J Schaetzle
(74) *Attorney, Agent, or Firm*—Oyen Wiggs Green & Mutala LLP

(57) ABSTRACT

A method of and an apparatus for monitoring the heart motion of a subject employ a probe which can be coupled to the aortic arch or to the thyroid cartilage of the subject for detecting movements caused by the heart motion and displaying the accelerations and displacement of the heart motion on an acceleration display and a displacement display. A mechanical motion amplifier amplifies the acceleration and an optical amplifier amplifies the displacement to counteract noise.

25 Claims, 15 Drawing Sheets

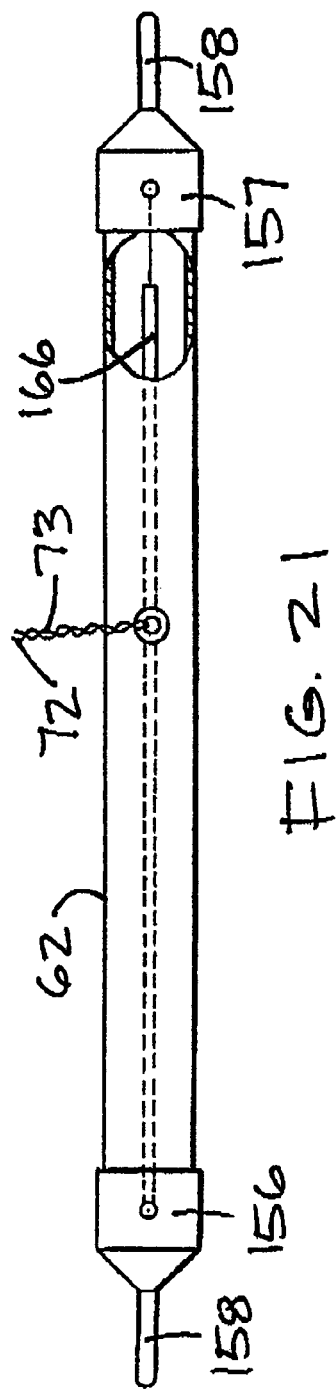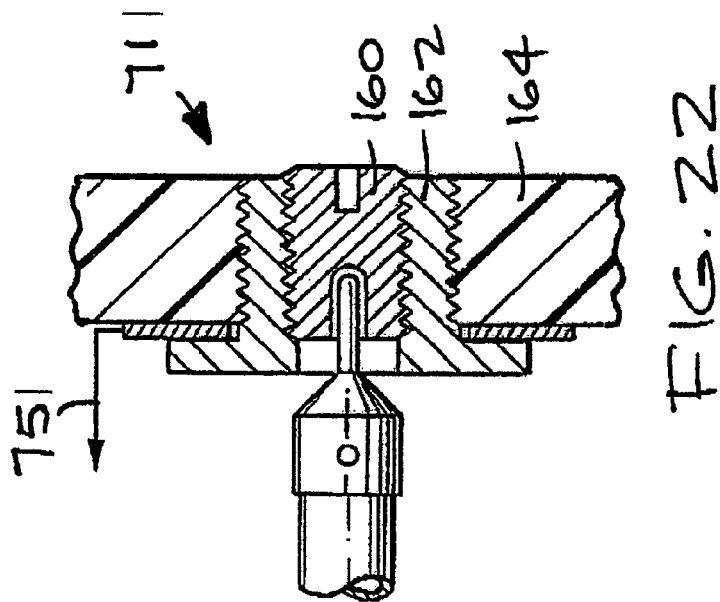

METHODS OF AND APPARATUS FOR MONITORING HEART MOTIONS

BACKGROUND OF THE INVENTION

1. Field of the Invention

The present invention relates to methods of and apparatus for non-invasively monitoring heart motion and is useful for the non-invasive monitoring of cardiac functions, in particular, but not exclusively, of human hearts.

2. Description of the Related Art

In the past, methods for the non-invasive monitoring of cardiac function have included:

Mechanical methods, for example, pulse recording of the jugular carotid artery or apex cardiography.

Electrical techniques, for example, electrocardiograms (ECGs).

Imaging techniques, including echocardiology, radiography and magnetic resonance imaging (MRI).

However, mechanical methods are inaccurate because of physical differences between subjects. For example, the intensity of heart sounds cannot be accurately measured because of the fat thickness layer differences.

Some non-invasive mechanical methods do not couple properly to the external movement generated by the heart and are therefore of little use.

The electrical techniques cannot correlate to the force of cardiac contraction and are therefore of little use, and imaging techniques are also subject to this problem. For example, an echocardiogram determines a ratio known as the "ejection fraction", which is a measure of cardiac performance which may or may not be related to the force of the heart's contraction. In a normally functioning heart, this relationship may hold true, but this finding is unreliable because the head pressure of the cardiovascular system is unknown.

None of the above-mentioned prior methods or techniques can accurately measure the isovolumic phase of the heart cycle, which is the most important parameter to measure in identifying coronary artery disease.

In U.S. Pat. No. 5,865,759, issued Feb. 2, 1999 to the present inventor, the disclosure of which is incorporated herein by reference, there is disclosed an apparatus and method to assess cardiac function in human being which employ a sensing mechanism positioned on the thyroid cartilage in the neck against the trachea for sensing a response of the thyroid cartilage to heart function.

While this prior patent disclosed a restraining system to hold the sensing mechanism in position, it was found that the apparatus is extremely sensitive to gravity because the force resulting from the weight of the sensing mechanism and a sensor restraining system varied in dependence on the vertical and horizontal position of the subject under test.

Consequently, a large cardiac force would decouple the sensing mechanism, so that a subsequent low magnitude force would be recorded poorly or not at all. These weak forces were so poorly recorded that very large electronic amplification was used, resulting in a poor signal-to-noise ratio and the recording of mostly noise. The poor coupling resulted in false data, which showed a poor correlation between the isovolumic contraction phase and the ejection phase of the heart cycle in nominal hearts, as shown by a clinical study. Another result was that the diastolic part of the cycle could not be recorded. This is a very important phase in which the passive inflow into the ventricles occurs and data relating to this phase could indicate the elasticity of the ventricular muscle. Furthermore, this prior apparatus was difficult to operate because positioning the sensor on the thyroid cartilage was difficult as elastic members forming parts of the restraining system had to be in tension balance to prevent the sensing mechanism from being moved to one side or another of the thyroid cartilage, causing erroneous data. Also, with this prior apparatus, mechanical interference caused by the sensor restraining system and an accelerometer forming part of the sensing mechanism contacted clothing, pillows, beards, fatty neck tissue, and in the case of a short neck contacted the chest, resulting in huge errors. Because no coupling apparatus was provided in this prior system, the addition of more sensors was not possible nor could reliable data be obtained. Also, this prior system employed wire connections extending directly to a recorder, resulting in stiffness and inertial effects due to interference of the wiring with the motion of the sensor.

BRIEF SUMMARY OF THE INVENTION

According to the present invention, apparatus for monitoring the heart motion of a subject comprises a probe movable in response to movements of the anatomy of the subject, an accelerometer movable with the probe, an acceleration display indicative of the acceleration of movements of the probe, and a mechanical motion amplifier between the probe and the acceleration display.

Preferably, the apparatus includes a displacement display indicative of the displacement of the movement and an optical motion amplifier between the probe and the displacement display.

When this apparatus is in use, the acceleration and the displacement of the heart motions are simultaneously displayed in real time and can be observed to detect any irregularities of the heart motion.

In a preferred embodiment of the invention, the mechanical motion amplifier comprises a lever supported on a mounting which serves as a fulcrum, the lever and the mounting being pivotable about a pivot axis in response to movements of the probe, which is provided at one end of an effort section of the lever. An accelerometer is provided on a load section of the lever, with the pivot axis between the probe and the accelerometer. Pivotable movement of the accelerometer on the lever in response to the movements of the probe is an amplification of the pivotation of the lever and, therefore, of the movements of the probe, which correspond to the movements of the subject's anatomy. The pivotal movement of the accelerometer is amplified when the ratio of the load section length divided by the effort section length is greater than one. Electrical amplification of the accelerometer output can be employed as required.

The optical motion amplifier, in this embodiment, is an optical device in the form of a mirror supported on the mounting and a laser light source directing light onto the mirror for reflection to the displacement display.

These mechanical and optical motion amplifiers have the advantage that they provide the displays with noise levels substantially less than when electronic amplifications alone are utilized.

In the preferred embodiment of the invention, the accelerometer is adjustable in position along the load section of the lever in order to correspondingly adjust the magnitude of its motion. This largely eliminates inter-instrument differences, and enables comparison of data results between centres of clinical research as well as greatly reducing the cost of quality control in the manufacturing process.

The apparatus also includes a chin rest which can be engaged with the subject's chin, with the probe adjusted to engage the subject's thyroid cartilage, and a jaw and head rest which can be engaged with the subject's jaw and head with the probe adjusted coupled with the arch of the subject's aorta in the region in the base of the brachiocephalic artery. In this way, the apparatus can be adjusted for engagement with either of these two parts of the anatomy of the subject.

BRIEF DESCRIPTION OF THE DRAWINGS

The invention will be more readily understood from the following description of an embodiment thereof given, by way of example only, with reference to the accompanying drawings, in which:

FIG. 21 shows a view in side elevation of a pivotable support member forming part of the apparatus of FIG. 1-4;

FIG. 22 shows a view taken in cross-section through a pivot supporting one end of the support member of FIG. 21 and electrically connecting the pivot to an analog-to-digital converter.

DESCRIPTION OF THE PREFERRED EMBODIMENT

Figure 1:
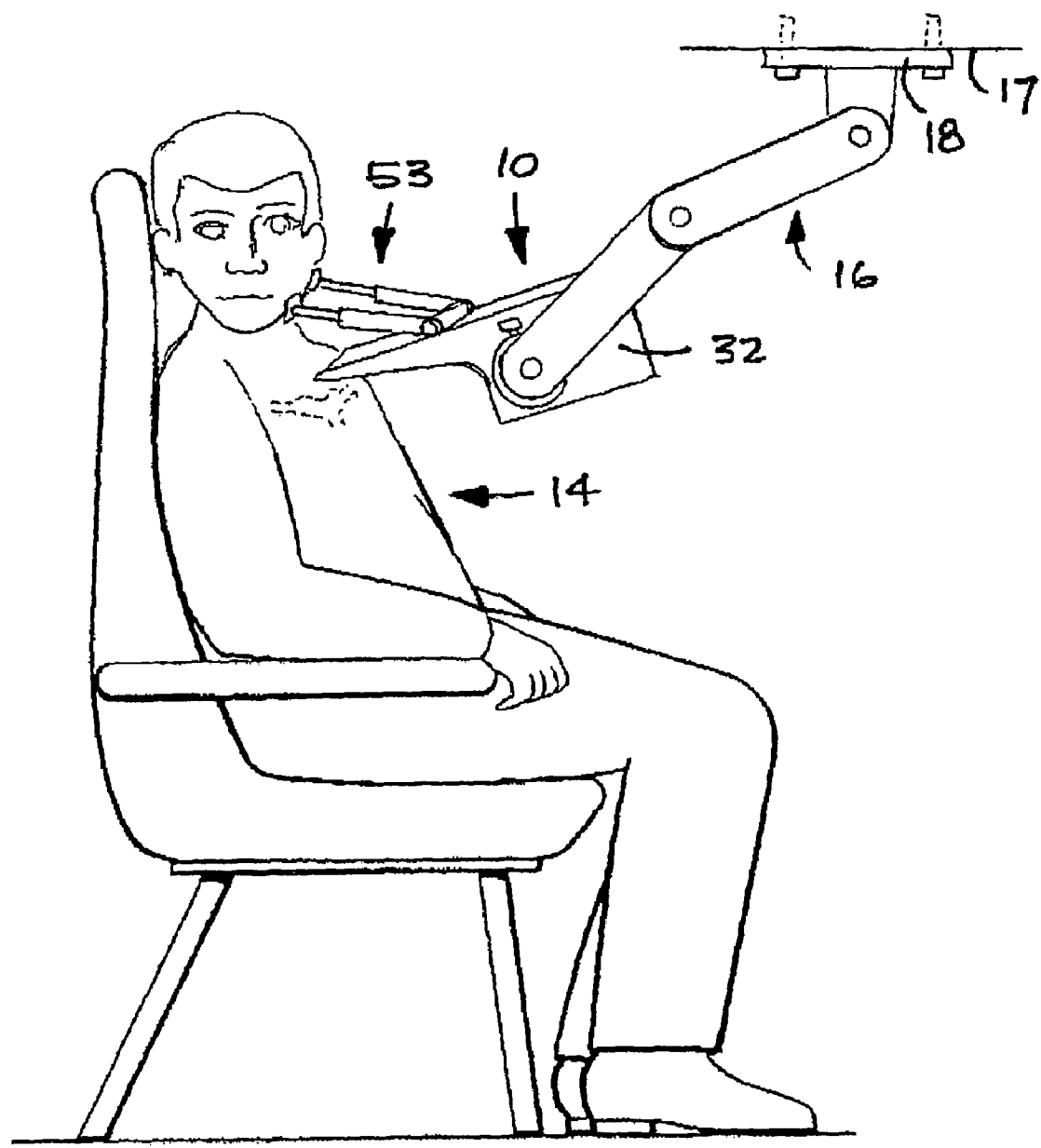
FIG. 1 shows a view in side elevation of a heart monitoring apparatus according to a preferred embodiment of the invention being coupled to the aortic arch of a seated subject.

To facilitate understanding of the various modes of operation of the apparatus of FIG. 1, which is a sensor apparatus indicated generally by reference numeral 10 in FIG. 1, the sensor apparatus 10 is shown in coupled relationship to subjects in different positions in FIGS. 1 to 4 of the accompanying drawings. Accordingly, FIGS. 1 to 4 will firstly be described below, before a more detailed description of the construction and operation of the sensor apparatus 10.

Measurement of the heart's motion, such as its acceleration, is important as the motion of the heart is a function of force which arises from a change in momentum of the heart mass and the ejection of blood during the various phases of the heart cycle. When a heart abnormality appears, the pattern and the amplitude of these forces change, thereby yielding diagnostic value.

The heart generates both strong and weak forces, which are all of importance in diagnosis. The method and apparatus described below enable the measurement of both systolic and diastolic phases of the heart cycle. As described below, the present apparatus can measure the heart forces generated at the brachiocephalic region of the aortic arch as well as those at the thyroid cartilage region of the trachea. The aortic arch is an ideal point to measure as it provides much information on all of the phases of the heart cycle and provides the most information on atrial contraction. It also is the best method for the operating room as the patient does not have to have his knees elevated close to his body nor does he have to elevate the head and bend it towards his chest. The present method enables coupling of the apparatus to the trachea so strongly that many different sensors can be used simultaneously, for providing displacement and acceleration waveforms in real time and for enabling a variety of sensors, including optic types, to be utilized. The strong coupling enables mechanical and optical amplification, thereby avoiding any need for high electronic amplification and drastically reducing the electronic noise so as to enable the recording of very small but important motions of the heart, e.g. that due to the passive inflow of blood into the ventricles. The shape and magnitude of recording can indicate the degree of elasticity of the left ventricular wall.

Using the present apparatus on normal hearts, the isovolumic phase (i.e. the hearts contraction before the valves of the heart are open) is strongly correlated to the ejection phase in magnitude and duration. The value of this is obtained in cases where the force of contraction is large but the ejection is of low magnitude, and allows a conclusion, with assurance, that stenosis of the aortic valve exists. The ejection fraction can be obtained at a fraction of the cost of an echocardiograph by constructing a nomogram. The procedure for effecting this is to firstly derive normal values for the amplitudes of the isovolumic and ejection phases of the heart cycle in a resting healthy adult. These values can then be equated to the value of the ejection fraction as determined by the electrocardiograph, which is known to be 67%. This value is equated to the isovolumetric amplitude and the ejection amplitude. The electrocardiograph identifies subjects with ejection fractions of 17% to 57%, which are equated to the values obtained by the present method and apparatus. The ejection fraction can now be obtained from the values of the isovolumic and ejection phases. Error can be prevented by not using data when there are indications of valve abnormalities, which are indicated when high values of the isovolumetric phase do not occur with high values in the ejection phase and vice versa.

There is some difficulty in interpreting the acceleration waveform, even if an ECG had been taken simultaneously. The present method solves this problem by simultaneously and in real time recording the displacement and acceleration waveforms. The direction of the acceleration, especially during the isovolumic phase, can be determined from the displacement, which enables diagnosis of paradoxical left ventricular motion, which is an indicator of cardiac muscle damage.

The present apparatus virtually eliminates inter-instrument differences, which are a large problem in acceleration measurements, as accelerometers vary in their outputs.

The present method and apparatus produce accurate results independently of the subject's physical structure, and resist any interference from clothing, beards etc. They are easily operable in an office, an emergency room or an operating room theater.

The use of the brachiocephalic area of the aortic arch is also ideal for cardiac research in most mammals.

In FIG. 1, the sensor apparatus 10 is shown in coupled relationship with the aortic arch of the chest of a subject seated in a chair indicated generally by reference numeral 14. The sensor apparatus 10 is carried by a support device, indicated generally by reference numeral 16, from a ceiling 17 by a support plate 18 so that the sensor apparatus 10 can be readily manoeuvred and adjusted in position relative to the subject 12.

Figure 9:
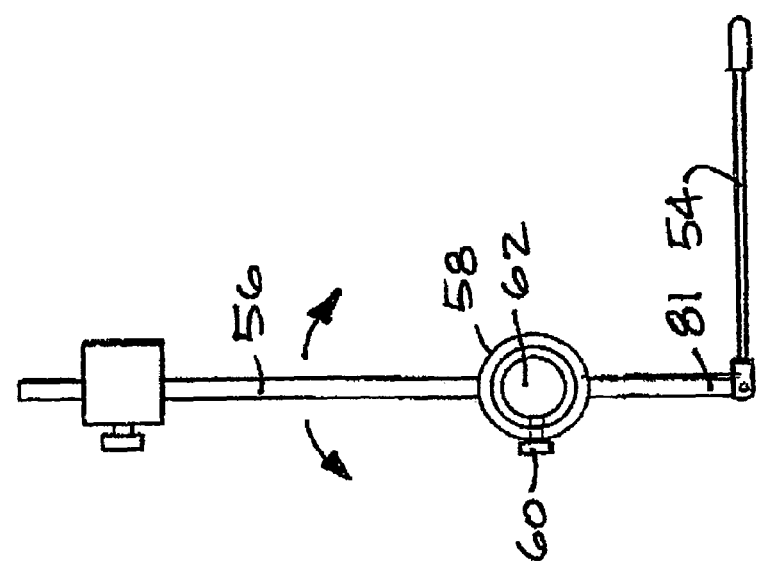
FIG. 9 shows a side view of the components of the apparatus shown in FIG. 8, with an aortic arch connected to the effort section of the lever for coupling to the aortic arch.

The sensor apparatus 10 is moved forward or backward as required to couple an probe of the sensor apparatus 10 directly behind the right-hand side of the manubrium, substantially parallel to the main axis of the heart, between the jugular and the clavicular notch and angled approximately 45° to the neck. The subject's head is rotated to the right. The subject is asked to inhale deeply several times to facilitate the movement of the probe to a depth greater than 1.5 inches until the probe reaches the aortic arch and a record is obtained. A jaw and head rest, indicated generally by reference numeral 53 and provided on a housing 32 of the sensor apparatus 10, is adjusted to contact the jaw and the base of the skull when contact is made with the brachiocephalic region of the arch of the aorta at a point approximately 2 inches below the manubrium, by an aortic arch 54 (FIG. 9) fitted onto an end of a lever 56 projecting from the housing 32, as described in greater detail below. As also described in greater detail below, correct coupling of the probe 54 with the subject's aortic arch in the brachiocephalic region will be indicated by a strong pivotal movement of the lever 56. The lung resistance can influence the motion of the heart and should therefore be measured prior to determining the performance of the heart. In this type of test, the subject is asked to breath fairly rapidly. The higher the amplitude of the displacement is, the higher the resistance of the lung is gauged to be.

Figure 2:
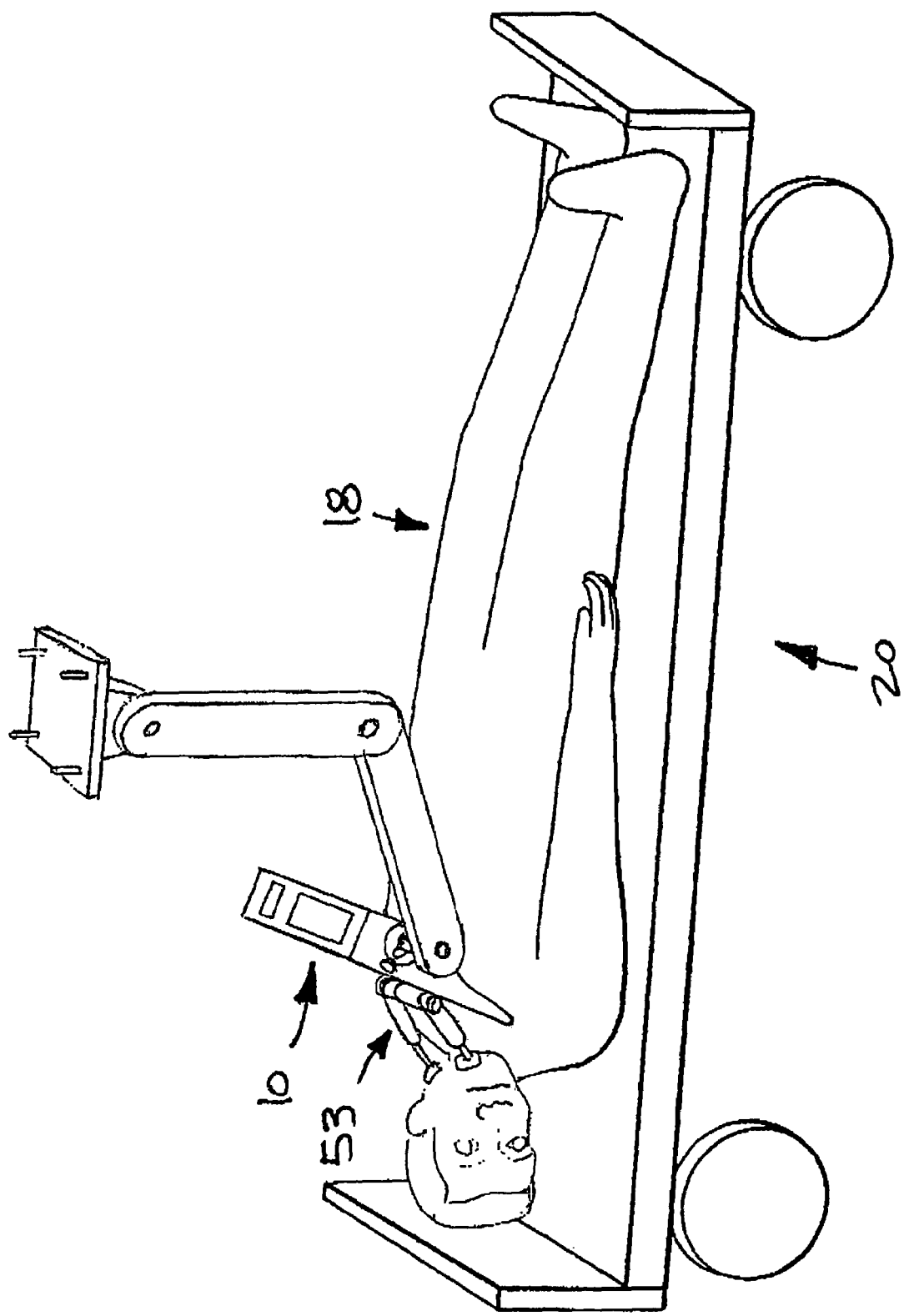
FIG. 2 shows a view in perspective of the apparatus of FIG. 1 coupled to the aortic arch of a subject in a prone position.

In FIG. 2, the sensor apparatus 10 is shown in use on a subject, indicated generally by reference numeral 18, who is lying in a prone position, with his head turned to the right, on a trolley indicated generally by reference numeral 20. The probe 54 is coupled to the aortic arch of the subject 18, while the jaw and head rest 53 is employed to position the sensor apparatus 10 relative to the subject.

Figure 3:
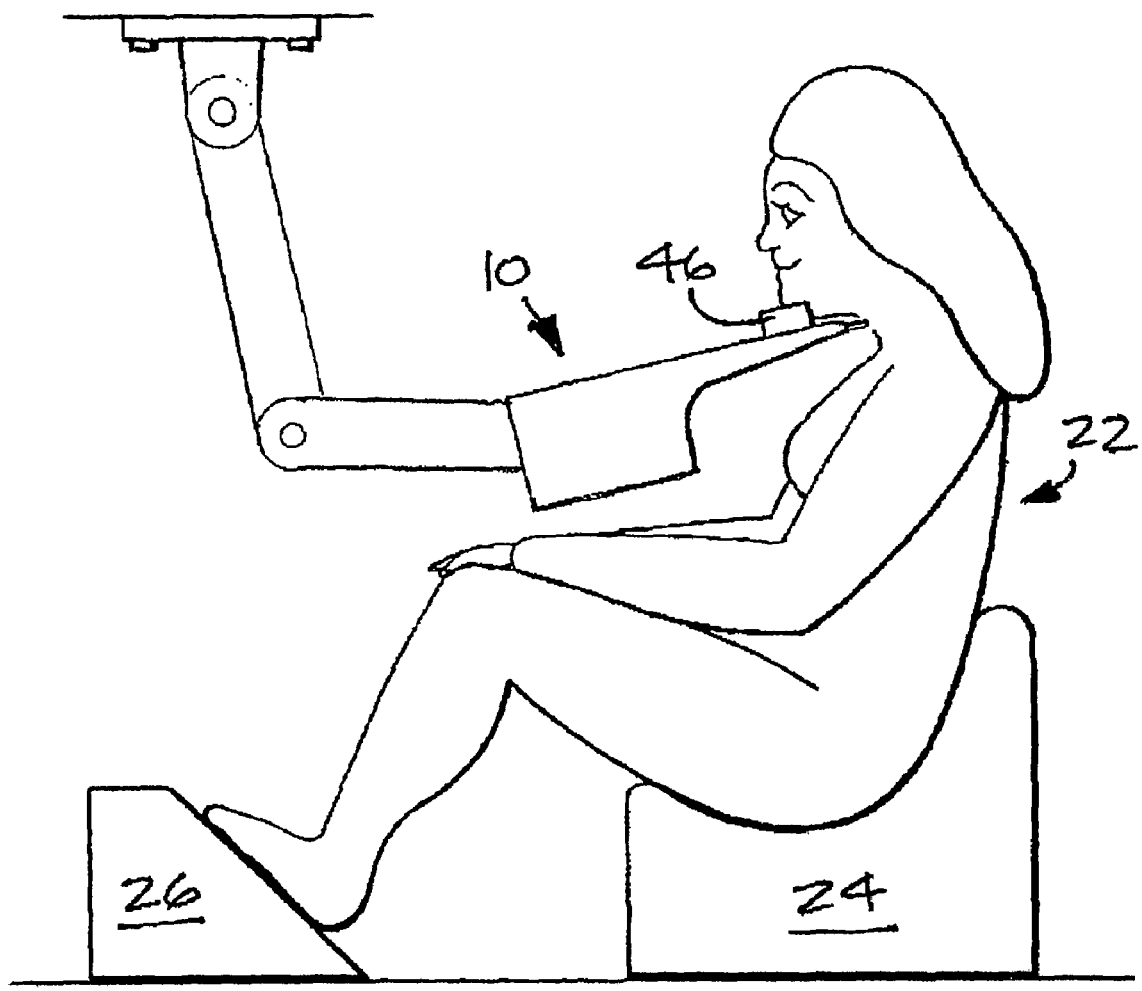
FIG. 3 shows a view in side elevation of the apparatus in FIG. 1 in use on a seated subject with the apparatus coupled to the thyroid cartilage of the subject.
Figure 10:
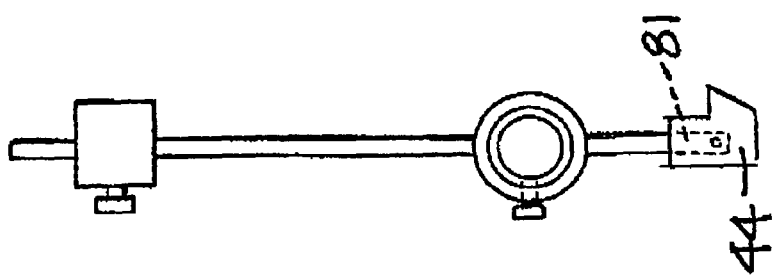
FIG. 10 shows a view corresponding to that of FIG. 9, but with the probe replaced by a different probe for coupling to the trachea.

In FIG. 3, the sensor apparatus 10 is shown coupled to the thyroid cartilage of a subject indicated generally by reference numeral 22. The subject is seated on a seat 24 with her feet on a foot rest 26. In this case, the jaw and head rest 53 is not in use, and instead a U-shaped chin rest 46 is engaged with the subject's chin to position the sensor apparatus 10 relative to the subject. Also, the probe 54 is replaced on the lever 56 by the probe 44 (FIG. 10).

In this mode, the subject's head is bent towards the chest and the feet raised close to the body to raise the pressure in the abdomen. The sensor apparatus 10 is then moved into position so as to exert a force against the trachea on the thyroid cartilage while at the same time the top of the sensor apparatus 10 is adjusted to be parallel to the jaw.

Figure 4:
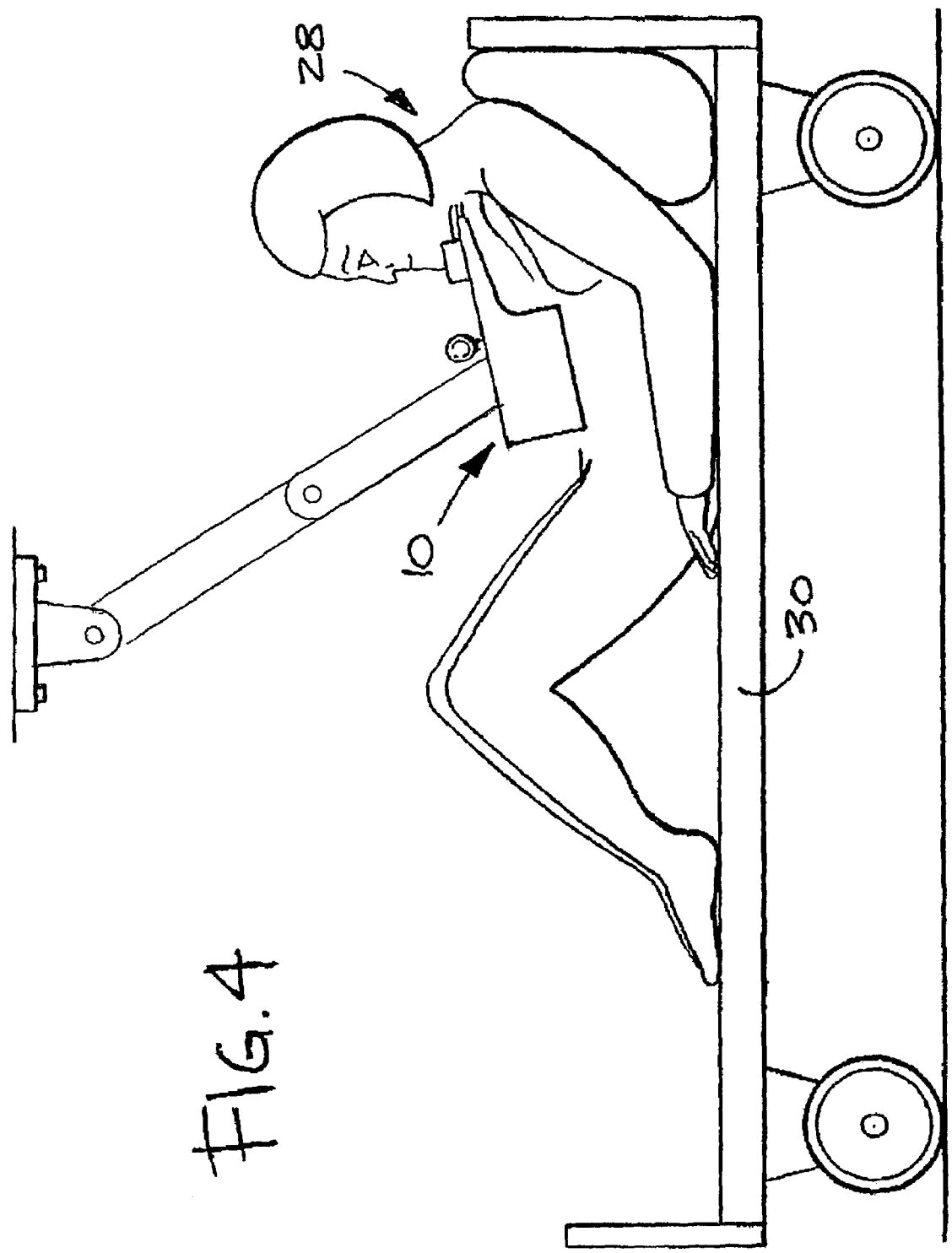
FIG. 4 shows a view in side elevation of the apparatus of FIG. 1 in use on a subject in a prone position with the device again coupled to the thyroid cartilage of the subject.

In FIG. 4, the sensor apparatus 10 is shown coupled by the probe 44 to the thyroid cartilage of a subject, indicated generally by reference numeral 28, who is in a semi-prone position by a trolley indicated generally by reference numeral 30.

The manner in which the sensor apparatus 10 can be adapted for use in the various positions shown in FIGS. 1 through 4 will be more readily apparent from the following description of the construction and operation of the sensor apparatus 10.

Figure 5:
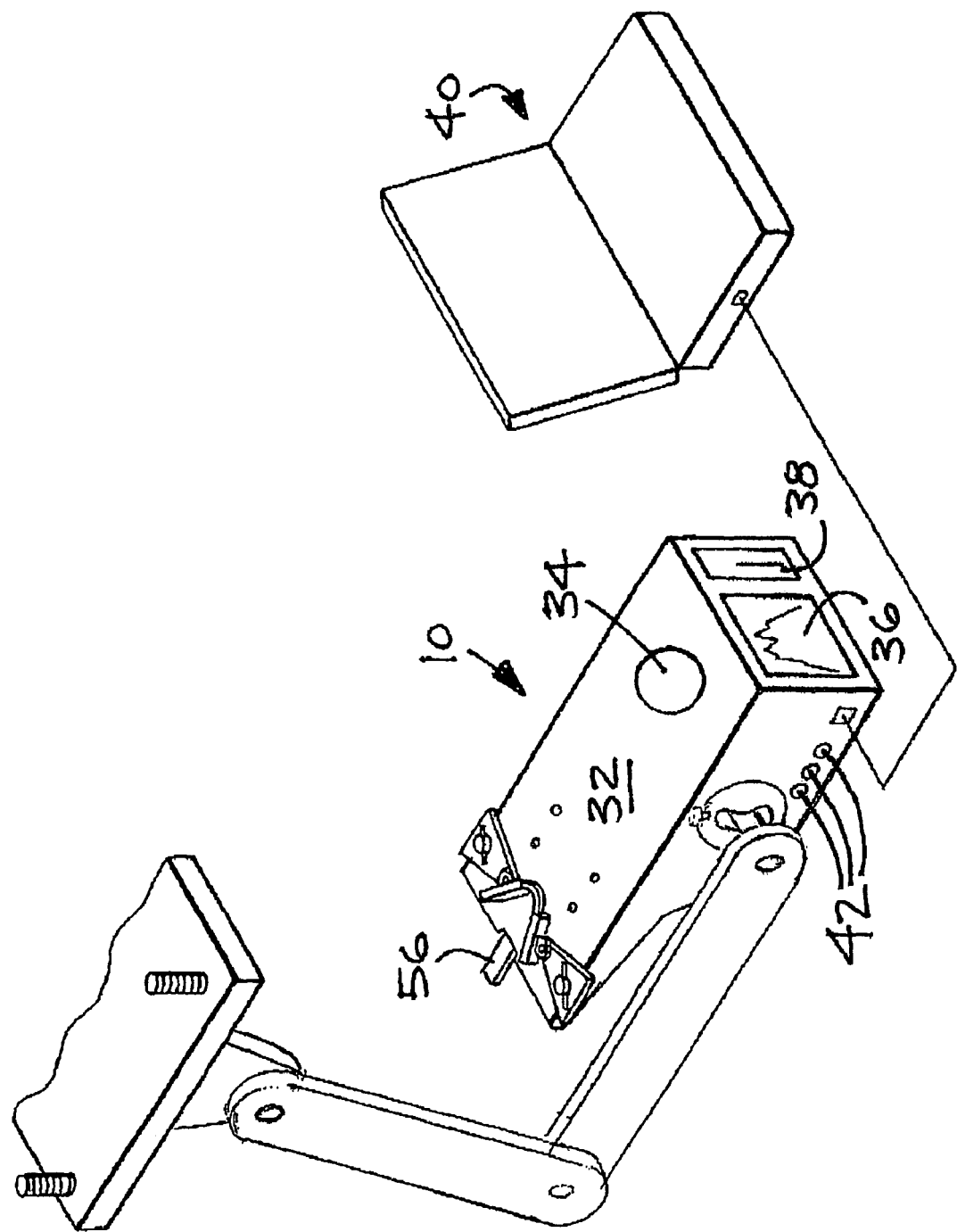
FIG. 5 shows a view in perspective parts of the apparatus of FIGS. 1-4.

As shown in FIG. 5, a manually engageable handle in the form of a ball 34, by means of which the sensor apparatus 10 can be manoeuvred in position, is provided on the housing 32, which is connected to the support device 16 by a ball joint 35, allowing the housing 323 to be tilted as desired. The ball joint 35 is provided with a lock screw 37 for fixing the housing 32 in position relative to the support device 16.

At one end of the housing 32, there is provided a displacement display 36 for displaying the waveform of the displacement of a subject's heart, and a displacement magnitude display 38 for displaying the magnitude of the displacement whose waveform is shown by the display 36.

Figure 23:
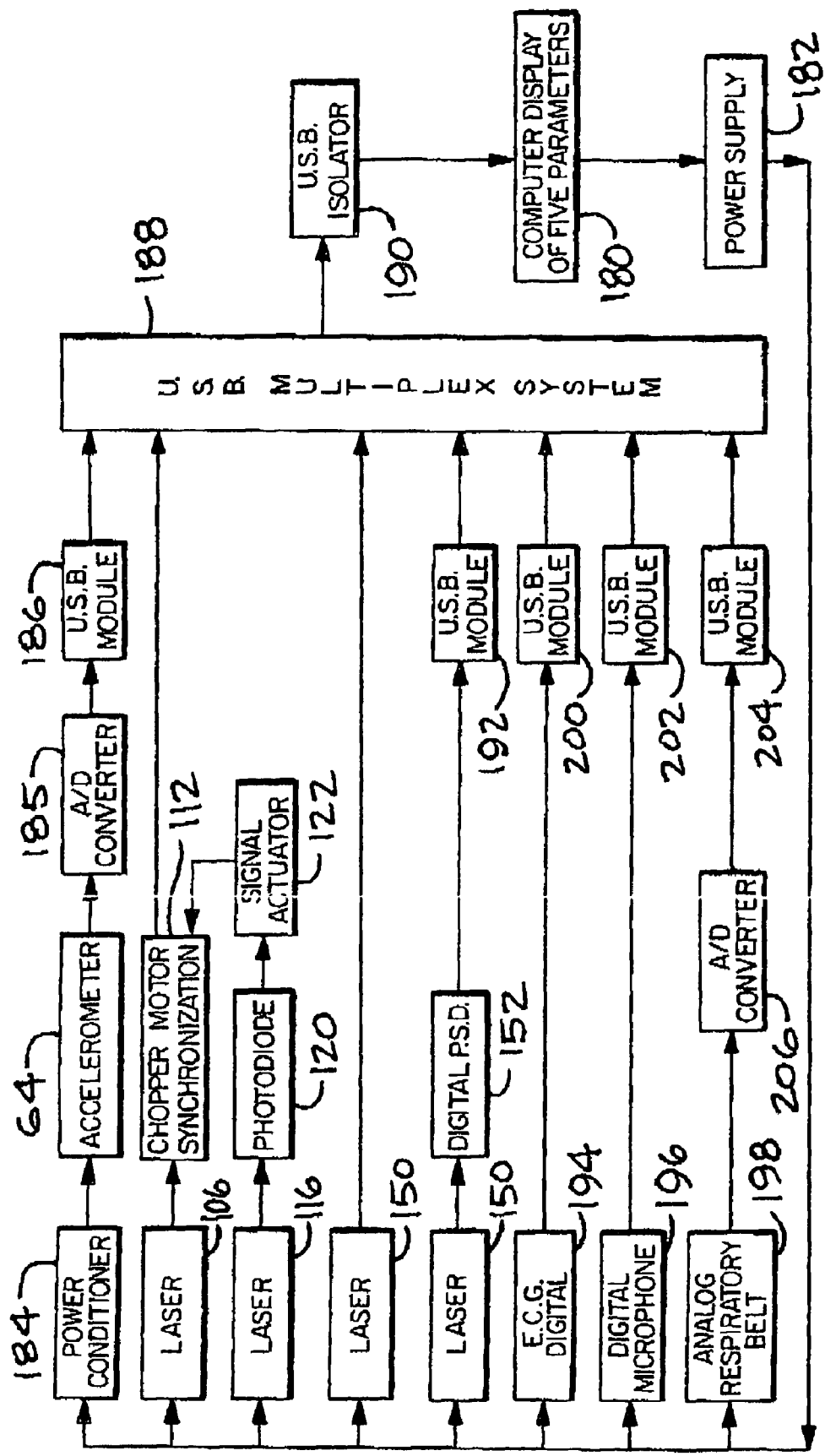
FIG. 23 shows a block diagram of the components of the apparatus of FIG. 1 with a system linkage to a computer using a USB multiplexing system.

The sensor apparatus 10 is connected to a laptop computer indicated generally reference numeral 40, and the housing 32 is provided with three sockets 42 for connecting a digital microphone 194, a digital ECG apparatus 194 and a digital respiratory belt 196, which are diagrammatically illustrated in FIG. 23 and which are associated in known manner with the subject to be monitored when the apparatus is in use.

Figure 6:
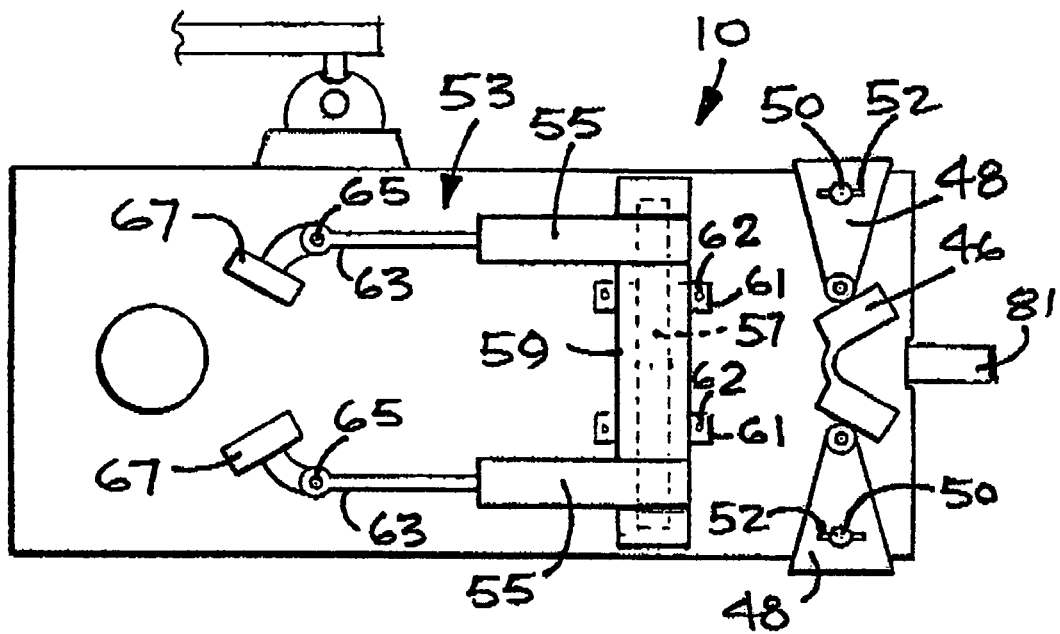
FIGS. 6 and 7 show plan views of parts of the apparatus of FIGS. 1-4, with a chin rest and a jaw and head rest.
Figure 7:
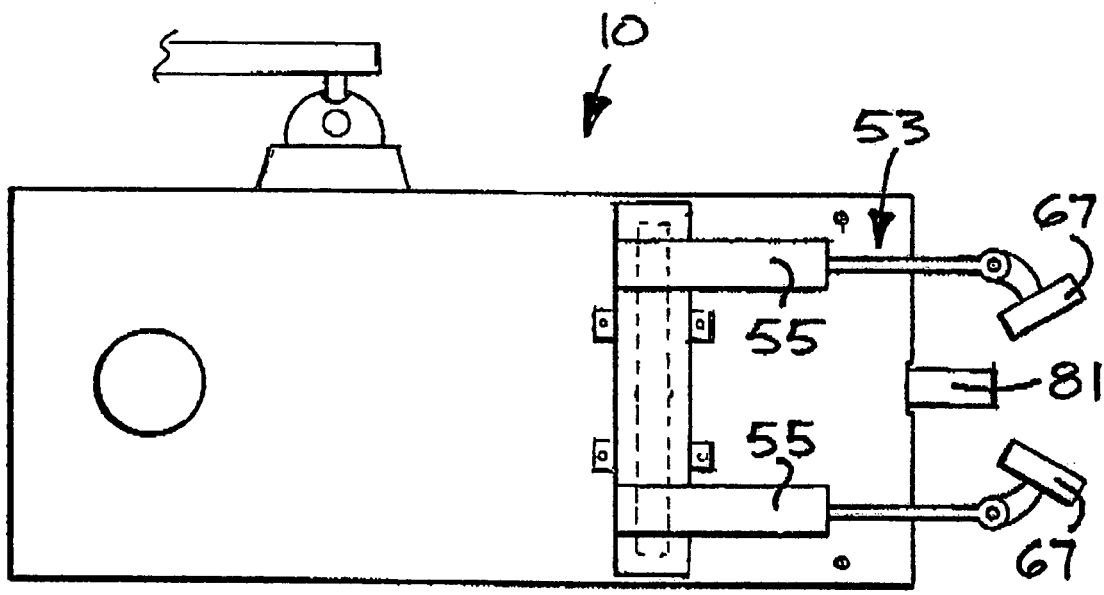

As shown in FIGS. 6 and 7, the jaw and head probe 53 has a pair of arms 55 which are each pivotally secured at one end to a shaft 57. The shaft 57 extends along the interior of a sleeve 59, which is secured on the housing 32 by lugs 61 extending from the sleeve 59 and secured by screws 62 to the housing 32. At its opposite, free end 63, each of the arms 55 is connected by a pivot 65 to a pad 67 which rests on the subject when the jaw and head rest 53 is in use. End caps 69 in threaded engagement with the ends of the shaft 57 retain the shaft 57 in position in the sleeve 59.

By pivoting the shaft 57 and the arms 55 relative to the housing 32, the jaw and chin rest 53 can be moved between an inoperative position, in which it is shown in FIG. 6 and in which the arms 55 lie above the housing 32, and an operative position, in which it is shown in FIG. 7 and in which the arms 55 and their pads 67 project beyond the end of the housing from which the lever 56 protrudes.

The jaw and head rest 53 is shown in use in FIGS. 1 and 2. Having the subject in the supine position as shown in FIG. 2 is an ideal arrangement for the operating room theatre, as the subject can lie flat on his or her back. The head should be turned to the right, as shown. The jaw and head rest 53 is pivoted so as to project forwardly from the housing 32 and the sensor apparatus 10 is manipulated into position and tilted, using the ball 34, to position the probe 54 just behind the right side of the manubrium, between the jugular and the clavicular notch and angled 45° towards the neck and substantially parallel to the main axis of the heart. The subject is asked to inhale deeply several times to facilitate the movement of the probe to a depth greater than 1.5 inches until the probe reaches the aortic arch and a record is obtained. The jaw and head rest 53 is adjusted for contact with the jaw and the base of the skull of the subject, thereby preventing interference with the motion of the probe 54.

Figure 11:
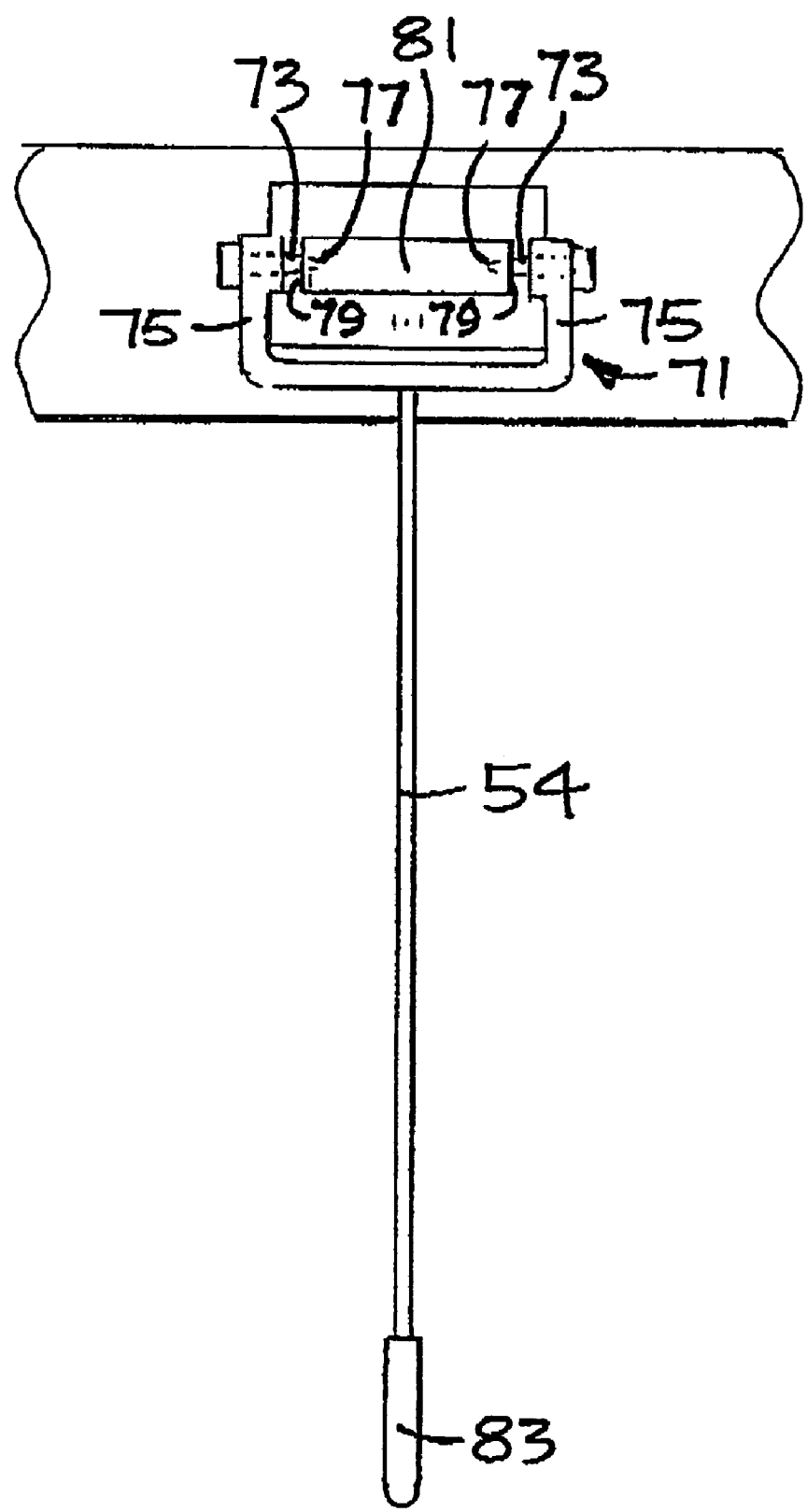
FIG. 11 shows a view in side elevation of the aortic arch of FIG. 9.

As shown in FIG. 11, the probe 54 is in the form of a rod which at one end has a bifurcated end portion indicated generally by reference numeral 71. A pair of pivot pins 73 in threaded engagement with arms 75 of the bifurcated end portion 71 have pointed ends 77 pressed into opposite longitudinal edges 79 of an end portion 81 of the lever 56, which projects from the housing 32, so as to pivotally secure the probe 54 to the lever 56.

In addition to the jaw and head rest 53, the chin rest 46 (FIG. 6) is provided on the housing 32 is employed when the sensor apparatus 10 is coupled to the thyroid cartilage, as shown in FIGS. 3 and 4.

By means of plates 48 pivotally connected to opposite sides of the chin rest 48 and adjustment screws 50, inserted through slots 52 in the plates 48 into threaded engagement with the housing 32, the chin rest 46 can be adjusted to contact the subject's chin. The screws 50 can then be tightened, after which the ball 34 is manipulated to move probe 44, which is fitted on the end portion 81 of the lever 56 as shown in FIG. 10, into contact with the brachiocephalic region of the arch of the aorta, which will be indicated by a strong pivotation of the support member 62. By unscrewing the screws 50, the chin rest 46, with its connection plates 48, can be removed from the housing 32.

By removing the chin rest 46 and pivoting the jaw and head rest 53 from the position in which it is shown in FIG. 6 to the operative position shown in FIG. 7, and by replacing the probe 44 on the lever 56 by the probe 54, the sensor apparatus 10 can be adapted for coupling to the aortic arch, as indicated above.

The lever 56 is mounted, by means of a mounting in the form of a bushing 58 (FIG. 9) and a locking screw 60, on a pivotal support member 62, the construction and operation of which are described in greater detail below. The probe 44 or 54, when the apparatus is in use, is displaced by movements of the relevant part of the subjects anatomy resulting from the subject's heart motion and these movements cause the lever 56 and the support member 62 to pivot about the longitudinal axis of the support member 62.

Figure 8:
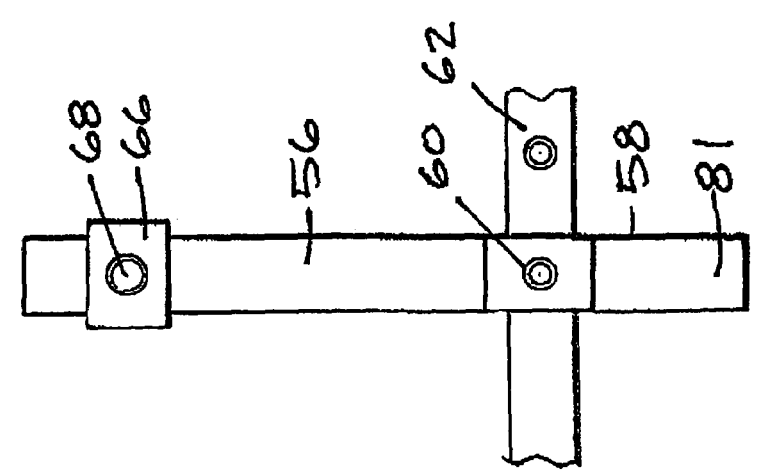
FIG. 8 shows a broken-away view of a lever and a pivotable support member pivotally supporting the lever.
Figure 8A:
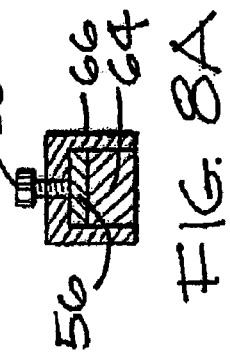
FIG. 8A shows a view taken in section along the line 8A-8A of FIG. 8.

An accelerometer 64 (FIG. 8a) is fixed to a U-shaped housing 66, and a locking screw 68 extends through the housing 66 in threaded engagement with the housing 66 for releasably securing the housing 66 and, therewith, the accelerometer 64 to the lever 56. The housing 66 and the screw 68 thereby provide an adjustable connection between the accelerometer 64 and the lever 56, which allows the position of the accelerometer 64 to be adjusted along the length of the lever 56 and, thereby, allows the amplification of the pivotation of the support member 62, in response to the movements of the probe 54 or 44, to be correspondingly adjusted. The output of the accelerometer 64 can thereby be calibrated so that the sensor apparatus 10 can be adjusted to take into account variations in the output of the accelerometer 64 and, also, the amplification of the pivotation of the support member 62 by the corresponding pivotation of the lever 56.

Figure 12:
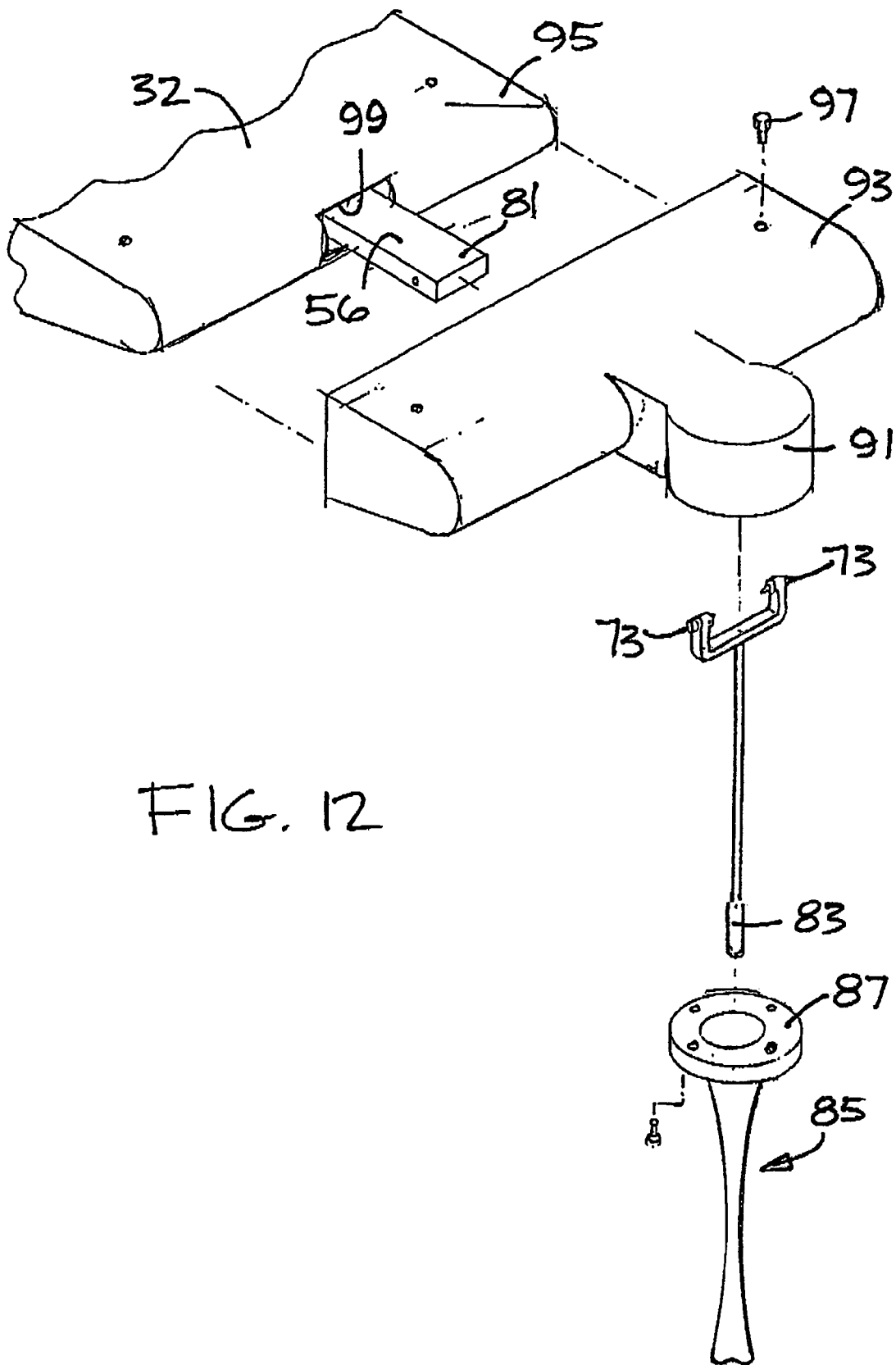
FIG. 12 shows a view in perspective of the aortic arch probe of FIG. 11 with a protective sheath and a broken-away part of a housing of the apparatus of FIGS. 6 and 7.

As shown in FIGS. 11 and 12, a removable protective sheath 83 is fitted over the probe 54 at its free end, opposite from the bifurcated end portion 71.

Figures 13, 14:
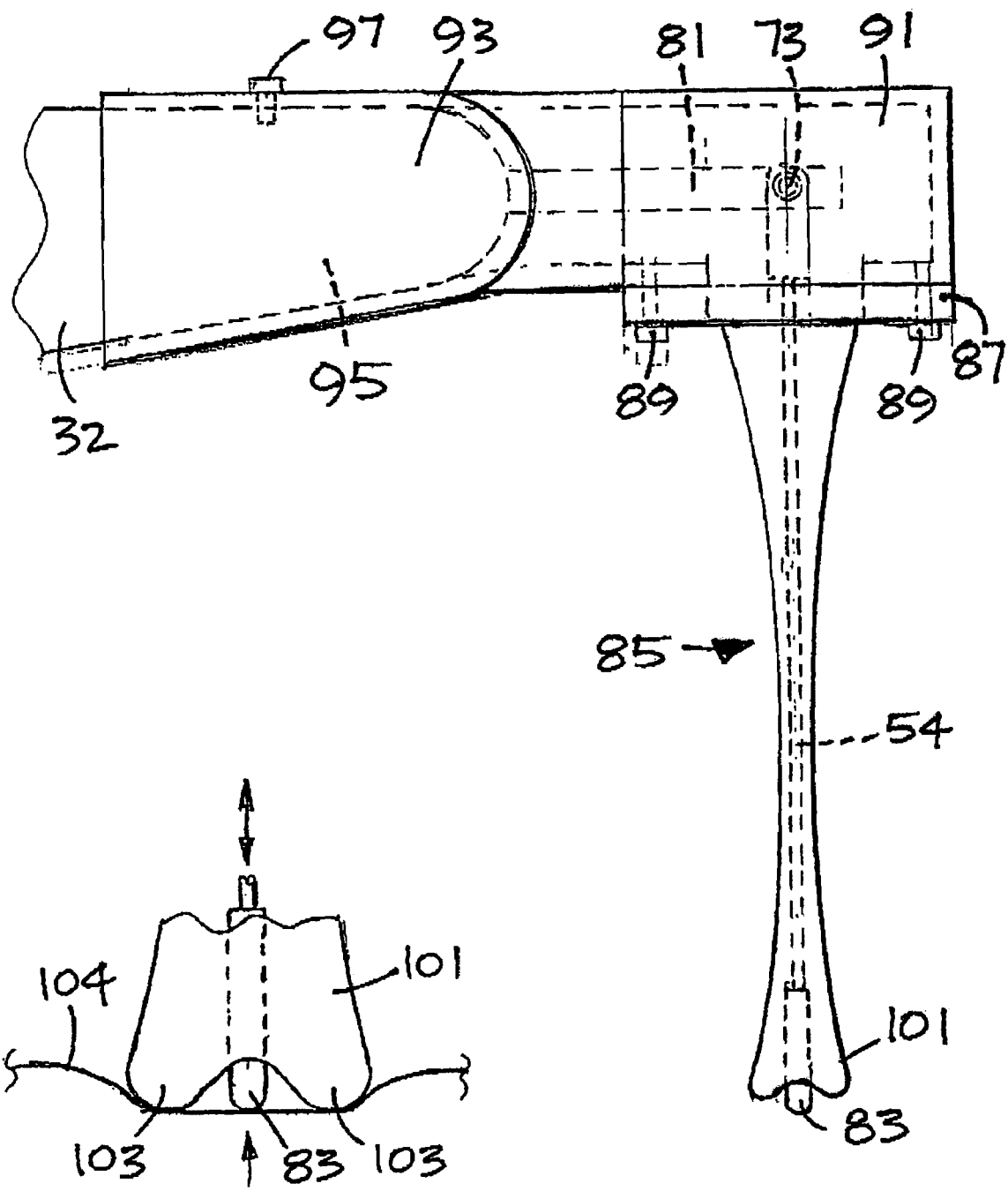
FIG. 13 shows a view in side elevation of the parts shown in FIG. 12.
FIG. 14 shows a broken-away view of an end of the aortic arch probe of FIGS. 11 and 12 and its protective sheath in coupling contact with the skin of a subject.

Referring now to FIGS. 12-14, the probe 54 is housed in an elongate protective housing indicated generally by reference numeral 85, which at its upper end has an annular end portion 87. By means of screws 89 inserted through the end portion 87 into threaded engagement with a protruding portion 91 of a housing 93, the housing 85 is releasably secured to the housing 93 The protruding end portion 81 of the lever 56 projects into the housing 93 into pivotal engagement with the pivot pins 73 within the protruding portion 91. The housing 93 is in turn secured over an end portion 95 of the housing 32 by screws 97 and the end portion 95 is formed with a rectangular opening 99 through which the end portion 81 of the lever 56 projects.

As shown in FIG. 14, the protective housing 85 has an open lower end portion 101, through which the tip of the sheath 83 protrudes, and is formed with end protrusions 103 at opposite sides of the open end portion 101.

When the probe 54 is in use, the sensor apparatus 10 instrument is carefully pushed downwardly until the protrusions 103, as shown in FIG. 14, stretch the subject's skin, indicated by reference numeral 104, sufficiently to couple the tip of the sheath 83, and thereby the probe 56, to the brachiocephalic region of the aortic arch, which is detected by moving the probe 54 and reinserting it until maximum displacement amplitude is observed on the displacement display 36. A record of the displacement and acceleration of the heart is taken along with a record of the lung resistance to air flow. The subject is asked to breathe rapidly for the lung test and the resultant magnitude of the displacement recorded or observed on the phosphorescent screen of the displacement display 36 at the front of the sensor apparatus 10. The larger the displacement, the higher is the lung resistance to air flow.

Figure 16:
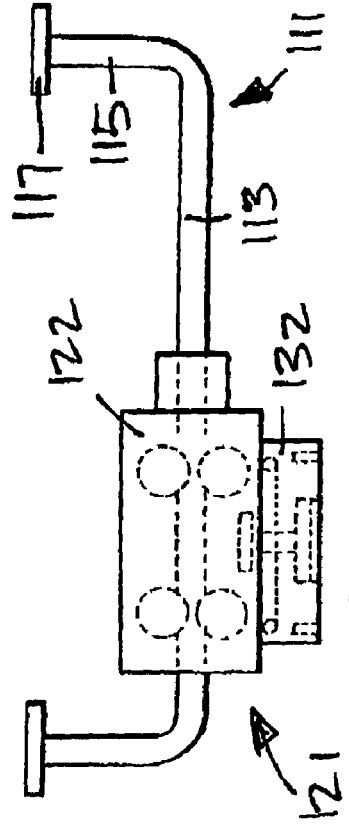
FIGS. 15 through 17 show a plan view, a view in side elevation and a view in transverse cross-section, respectively, of an overhead carriage and swivel mechanism forming part of the apparatus of FIGS. 1-4.
Figure 17:
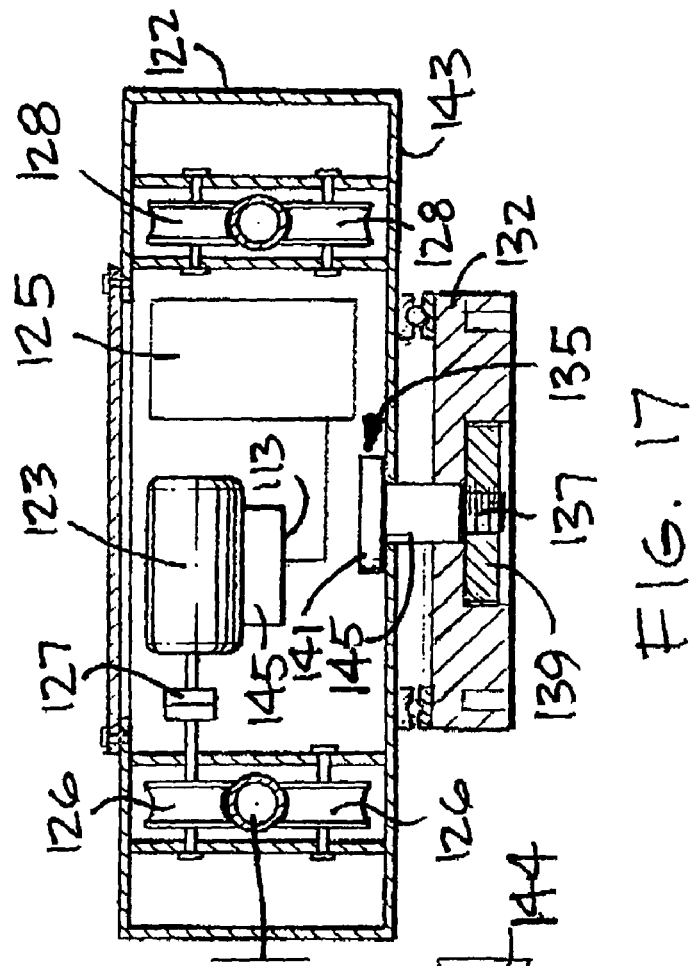
Figure 15:
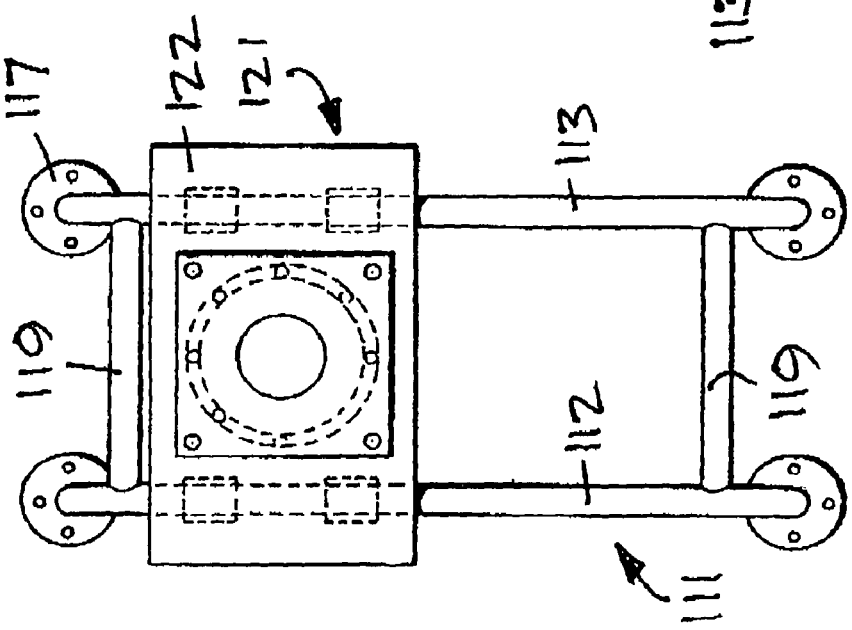

The support device 16, which comprises an overhead carriage and swivel mechanism of a type similar to that employed by dentists to support adjustable overhead lamps, is of a well known construction and will therefore not be described in greater detail herein. However, the support device 16, instead of being carried by the support plate 18 from the ceiling 17, may instead be mounted under an overhead carriage and swivel mechanism indicated generally by reference numeral 111 in FIGS. 15-17. The mechanism 111 has a pair of parallel rails 113, which as can be seen from FIG. 16 have upturned end portions 115 terminating in mounting brackets 117, by means of which the rails 113 can be secured by screws (not shown) to the ceiling 17. The rails 113 are braced by cross-bars 119 spaced apart along the rails 113 and a carriage indicated generally by reference numeral 120 is movable along the rails 113 between the cross-bars 119. The carriage 120 has a housing 122 containing an electric motor 123, a battery pack 125 for supplying power to the electric motor 123 and two pairs of rollers 126 and 128 in rolling engagement with the rails 113, one of the rollers 126 being connected through a friction clutch 127 to the electric motor 123 so that on energization of the motor 123 the carriage is driven along the rails 113.

A rotatable support plate 132 is mounted beneath the housing 122, by means of a threaded retainer, indicated generally by reference numeral 135, with a ball race 133 between the support plate 132 and the housing 122. The threaded retainer 135 has a threaded lower end 137 in threaded engagement with a nut 139 recessed in the underside of the support plate 132, a head 141 seated on a bottom wall 143 of the housing 122 and a cylindrical portion 145 between the threaded lower end 137 and the head 141. The retainer 135 is rotatable, together with the support plate 132, relative to the housing 122.

The energization of the motor 124 is controlled by a wireless remote control unit 144 communicating with a control unit 145 in the housing 122. The support plate 18 (FIG. 1) is secured by screws to the underside of the support plate 132, so that, after the housing 122 has been suitably positioned along the rails 113, the sensor apparatus 10 can be manually manoeuvred into position relative to the subject to be monitored.

Figure 18:
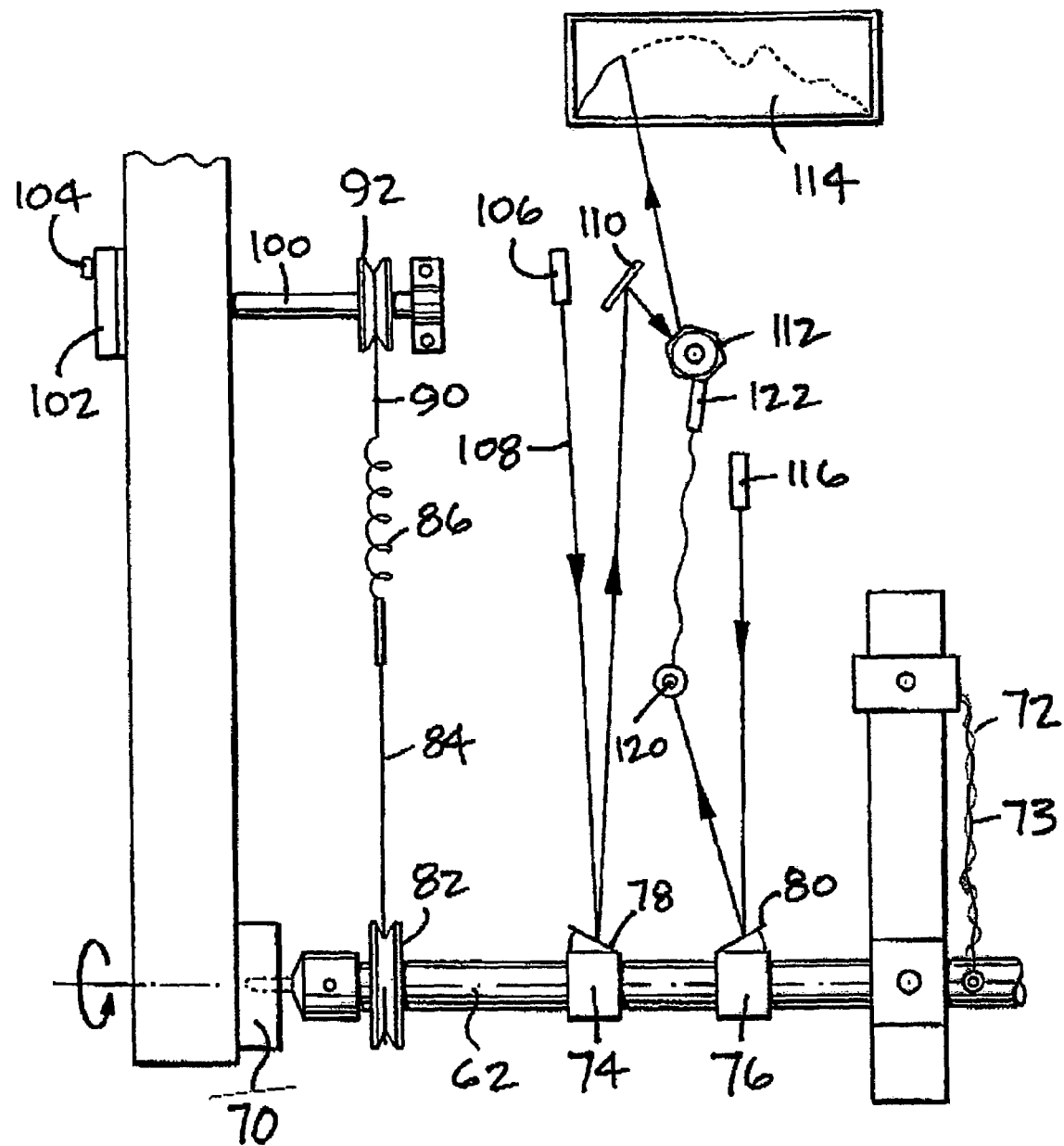
FIG. 18 shows a diagrammatic view of parts of the apparatus of FIGS. 1-4, including mechanical and optical motion amplifying devices.

From FIG. 18, it can be seen that the support member 62 is an elongate member, one end of which is journalled in a pivotal support 70. The opposite end of the support member 62, as shown in FIG. 22, is journalled in a pivotal support indicated generally by reference numeral 71, which is similar to the pivotal support 70. A pair of electrical conductors 72 and 73 connect the accelerometer 64 to the interior of the support member 62, as will be described in greater detail below with reference to FIG. 22. In addition, the pivotal support member 62 carries two mountings 74 and 76, on which mirrors 78 and 80 are mounted, and a pulley 82. The pulley 82 is connected by a cord 84 to one end of a helical tension spring 86, the opposite end of which is connected to a cord 90, wound on a pulley 92. The pulley 92 is mounted on a shaft 100, which is journalled in a side wall 88 of the housing 32 and which can be rotatably adjusted, by rotation of a manually adjustable detent knob 102 on the shaft 100, to exert an adjustable bias on the support member 62 and thereby to urge the probe 44 or 54 on the lever 56 towards the subject being monitored so as to assist in coupling the probe to the subject. The adjustment knob 102 can be releasably locked into position by means of a lock screw 104.

A laser light source in the form of a laser 106 directs a light beam 108 onto the mirror 78, from which the light beam is reflected onto a mirror 110 and a rotating mirror 112 to a display screen 114 forming part of the display 36 of FIG. 5. The screen 114 is a phosphorescent screen of high persistence, and the trace of the light beam 108 on the screen 114 represent the waveform of the displacement of the heart function being monitored.

A second laser 116 directs a light beam 118 onto the mirror 80, from which the light beam is reflected onto a photodiode 120 to control the energization of a motor 122 rotating the mirror 112, so that the rotation of the mirror 112 is synchronized with the pivotation of the pivotable support member 62 and, thus, the probe 44 or 54.

The pivotable support member 62 also carries a mounting 124 (FIG. 19) carrying a mirror 146 for reflecting a light beam 148 from a laser 150 onto a screen 152, which forms part of the display 38, and which is a phosphorous screen of long duration for displaying the magnitude of the displacement of the heart function.

The screen 152 may be replaced by a position sensing diode array 154 (FIG. 20), which provides a digital output having a magnitude corresponding to the deflection of the beam 148 by the pivotation of the mirror 146.

FIG. 21 shows in greater detail the pivotal support member 62 which is tubular and provided at opposite ends with end caps 156 and 157 from which protrude pivot pins 158. As illustrated by the pivotal connection 71 of FIG. 22, each pivot pins 158 is pivotally received in a threaded grub screw 160 in threaded engagement with a threaded retainer 162 which, in turn, is in threaded engagement with a wall 164 of the housing 32. The conductor 72 from the accelerometer 64 extends along the interior of the tubular pivotal member 62 to the right-hand end cap 157, as viewed in FIG. 21, which is electrically conductive and which electrically connects the conductor 72 through the grub screw 160 to an electrical conductor 75, thereby providing an electrical connection without affecting the pivotation of the pivotal member 62. The electrical conductor 75 is connected to the laptop computer 40. Similarly, the conductor 73 is connected though the left-hand end cap 158 to the computer 40. Within the tubular member 62, the conductors 72 and 73 extend along the interior of a tubular shield 166 which is soldered to the end cap 156 at the left-hand end of the pivotal support member 62, as viewed in FIG. 21.

FIG. 22 diagrammatically illustrates the processing of the dat obtained by the above-described apparatus. A computer display 180, which is the display of the laptop computer 40 (FIG. 1), displays images corresponding to those of the displacement and magnitude displays 36 and 38. The laptop computer 40 includes a power supply 182 for supplying power to the components of the sensor apparatus 10. More particularly, the power supply 182 supplies power through a power conditioner 184 to the accelerometer 64, the output of which is connected through an analog-to-digital converter 185, a USB module 186, a USB multiplexor 188 and a USB isolator 190 to the computer 40 to be shown on the display 180.

The lasers 106, 116 and 150 are also powered by the power supply 182. The beam of the laser 106, deflected by the mirror, and synchronised by the output of the diode 120, is supplied as a displacement waveform, which corresponds to that displayed on the displacement display 36, is supplied through the USB multiplex system 188 and the USB isolator 190 to be displayed on the display 180 in the form of a graph similar to that of the displacement display 36. The beam of the laser 116, falling on the photodiode 120, actuates the motor 122 to rotate the mirror 112 and thereby to synchronise the displacement display with the pivotation of the support member 62.

Figure 19:
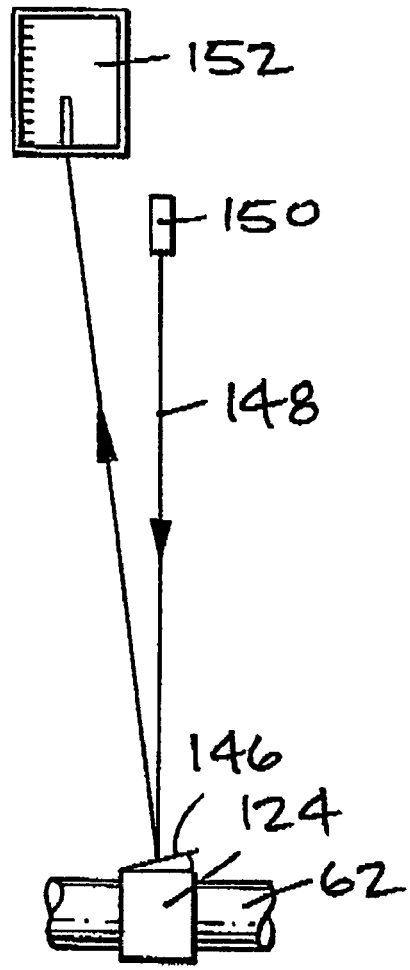
FIGS. 19 and 20 diagrammatically illustrate two modifications of an optical motion amplifying device shown in FIG. 12.

As indicated above, the laser 150 can be employed with the screen 152 or with the position sensing diode array 154, and is therefore shown twice in FIG. 23. When the laser 150 is used with the screen 152, as illustrated in FIG. 19, the beam of the laser 150, deflected by the mirror 146, provides an output signal representing the magnitude of the displacement, corresponding to that displayed on the display 38, which is supplied through the USB multiplex system 188 and the USB isolator to the laptop computer 40 to be shown on the display 180.

Figure 20:
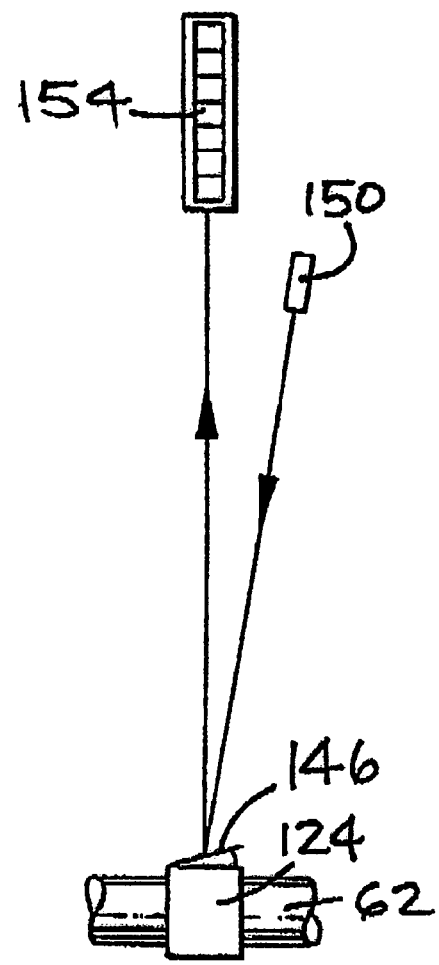

When, however, the deflected beam of the laser 154 is applied to the position sensing diode array 154, as illustrated in FIG. 20, the output of the position sensing diode display 154 is supplied through a USB module 192, the multiplex system 188 and the USB isolator 190 to be shown on the computer display 180.

FIG. 23 also shows the digital microphone 194, the digital ECG apparatus 194 and the digital respiratory belt 196 connected to respective USB modules 200, 202 and 204, with an analog-to-digital converter 206 connected between the analog respiratory belt 198 and the USB module 204. The USB modules 200, 202 and 204 are connected through the USB multiplex system 188 and the USB isolator 190 to the computer 40 so that their outputs can be displayed on the computer display 180.

It is an advantage of the apparatus described above with reference to the accompanying drawings that at least six cardiac parameters may be simultaneously recorded, i.e. the acceleration, displacement, the ECG, the phonocardiogram, and the respiratory cycle. The above-described apparatus records simultaneously and in real time the acceleration and the displacement waveforms, thereby making it possible to determine the direction of the acceleration at each phase of the heart cycle and enabling the diagnosis of many heart conditions, including paradoxical left ventricular motion which indicates cardiac muscle damage. The present apparatus can utilizes a variety of sensors to measure displacement, e.g. the miniature linear potentiometer, and the optical methods The optical motion amplifier shown in FIG. 12 can quickly display, without the aid of a computer or any other recording means, a high lung resistance indicative congestive heart failure. The present apparatus maintains its pre-exercise position and can be repositioned by remote control and is therefore suitable for operating theater use.

The present invention enables waveforms of cardiac motions to be obtained non-invasively from two different body sites, i.e. from the aortic arch and the trachea, and to be combined into a single resultant waveform, using the ECG as a phase marker, thereby providing more detailed diagnostic information than can be obtained from a single body site. The two waveforms can be independently analyzed and compared with one another and also with the resultant waveform.

The present invention may also be applied to animal research to determine the effect of experimental cardiac drugs on the heart.

As will be apparent to those skilled in the art, various modifications may be made in the above-described embodiment of the present invention within the scope of the appended claims.

I claim:

1. Apparatus for non-invasively monitoring the heart motion of a subject, comprising:
    a probe adapted to be coupled to the subject and displaced in response to the heart motion of the subject;
    an accelerometer responsive to displacement of the probe by the heart motion of the subject;
    a mechanical motion amplifier between the probe and the accelerometer;
    an acceleration display connected to an output of the accelerometer; and
    a displacement display connected to the mechanical motion amplifier for indicating the displacement of the probe.

2. Apparatus as claimed in claim 1, wherein the mechanical motion amplifier comprises a lever, the lever having an effect section and a load section, a mounting supporting the lever, the lever and the mounting being pivotable about a pivot axis in response to the displacement of the probe by the heart motion of the subject, the probe being at one end of the effect section of the lever, and the accelerometer being provided on the load section of the lever, with the pivot axis between said one end and the accelerometer.

3. Apparatus as claimed in claim 2, including means for applying a torque to the mounting to bias the probe against the subject.

4. Apparatus as claimed in claim 1, including a pivotable support member, the probe being connected to the support member for causing pivotation of the support member corresponding to the displacement of the probe in response to the movements of the anatomy of the subject, the mechanical motion amplifier comprising a lever arm mounted on the support member, and the accelerometer being provided on the lever arm.

5. Apparatus as claimed in claim 4, including pivots pivotally supporting the support member, the apparatus including an electrical connection between the accelerometer and the acceleration display and the electrical connection extending through the pivots.

6. Apparatus as claimed in claim 4, including an adjustable connection between the lever and the accelerometer, the adjustable connector allowing adjustment of the position of the accelerometer along the lever for varying its motion to thereby vary its output to calibrate the apparatus.

7. Apparatus as claimed in claim 1, including a jaw and head rest engageable with the subject's jaw and head for positioning the probe against the subject's aortic arch in the region of the base of the brachiocephalic artery.

8. Apparatus as claimed in claim 7, including a chin rest engageable with the subject's chin for positioning the probe against the subject's thyroid cartilage.

9. Apparatus as claimed in claim 1, including a chin rest engageable with the subject's chin for positioning the probe against the subject's thyroid cartilage.

10. Apparatus as claimed in claim 1, wherein the probe is adapted for coupling the apparatus to the aortic arch of the subject.

11. Apparatus as claimed in claim 1, wherein the probe is adapted for coupling the apparatus to the thyroid cartilage of the subject.

12. Apparatus as claimed in claim 1, including a displacement display indicative of the displacement of the probe and an optical motion amplifier between the probe and the displacement display.

13. Apparatus as claimed in claim 12, wherein the optical motion amplifier comprises a mirror mounted on the support member, and a laser light source directed onto the mirror, the displacement display being in a path of light reflected from the mirror.

14. Apparatus as claimed in claim 13, wherein the displacement display comprises a phosphorescent screen in the path of reflected laser light.

15. Apparatus as claimed in claim 1, including a protective shield around the probe, the shield having an open end, the probe having a free end protruding from the open end of the shield and the open end of the shield forming a skin engagement shield portion for engaging and stretching the subject's skin.

16. Apparatus as claimed in claim 15, wherein the mechanical motion amplifier comprises a lever and a lever mounting supporting the lever for pivotation of the lever, the accelerometer being mounted on the lever and the probe extending from the lever.

17. Apparatus for monitoring the heart motion of a subject, comprising:
    a probe adapted to be coupled to the subject and displaced in response to the heart motion of the subject;
    a displacement display indicative of the displacement of the probe; and
    an optical motion amplifier connecting the probe and the displacement display, including a spring exerting a torque on the mounting to bias the probe against the subject.

18. Apparatus for monitoring the heart motion of a subject, comprising:
    a probe adapted to be coupled to the subject and displaced in response to the heart motion of the subject;
    a displacement display indicative of the displacement of the probe; and
    an optical motion amplifier connecting the probe and the displacement display including;
    a pivotable support member;
    the probe being connected to the support member for causing pivotation of the support member corresponding to the displacement of the probe by the heart motion of the subject;
    an accelerometer responsive to displacement of the probe by the heart motion of the subject;
    a mechanical motion amplifier between the probe and the accelerometer; and
    an acceleration display connected to an output of the accelerometer.

19. Apparatus as claimed in claim 18, wherein the mechanical motion amplifier comprises a lever arm mounted on the support member, and means are provided for adjusting the accelerometer in position along the lever arm to correspondingly adjust the output of the accelerometer.

20. Apparatus for monitoring the heart motion of a subject, comprising:
- a probe for coupling the apparatus to the subject so that the probe is displaced in response to the heart motion of the subject;
- means responsive to displacement of the probe;
- the means responsive to the displacement of the probe comprising a mechanical motion amplifying mechanism for amplifying the displacement to generate outputs corresponding to acceleration of the heart motion and optical motion amplifying means for amplifying the movements to provide an amplification of the displacement of the heart motion; and
- first and second means responsive to the mechanical motion amplifying mechanism and the optical motion amplifying means, respectively, for displaying the amplitude and displacement of the heart motion.

21. Apparatus as claimed in claim 20, wherein the means responsive to the displacement of the probe include means pivotable in response to the displacement and the motion amplifying mechanism comprises means for amplifying pivotal movements of the pivotable means.

22. Apparatus as claimed in claim 20, wherein the probe comprises means for coupling the apparatus to the aortic arch of the subject.

23. Apparatus as claimed in claim 20, including a protective shield around the probe, the shield having an open end, the probe having a free end protruding from the open end of the shield and the open end of the shield forming a skin engagement shield portion for engaging and stretching the subject's skin.

24. Apparatus as claimed in claim 23, wherein the mechanical motion amplifier comprises a lever and a lever mounting supporting the lever for pivotation of the lever, the accelerometer being mounted on the lever and the probe extending from the lever.

25. Apparatus as claimed in claim 20, wherein the probe comprises means for coupling the apparatus to the thyroid cartilage of the subject.

* * * * *